United States Patent
Takai et al.

(10) Patent No.: US 10,101,345 B2
(45) Date of Patent: Oct. 16, 2018

(54) TEST STRIP PICKUP MECHANISM, TEST STRIP MOVING APPARATUS, LIQUID SAMPLE ANALYZER, AND TEST STRIP PICKUP METHOD

(71) Applicant: Sysmex Corporation, Kobe-shi, Hyogo (JP)

(72) Inventors: Satoshi Takai, Osaka (JP); Hanako Yura, Osaka (JP); Shingo Hatada, Osaka (JP); Yasuhiro Miyake, Osaka (JP)

(73) Assignee: SYSMEX CORPORATION, Kobe, Hyogo (JP)

(*) Notice: Subject to any disclaimer, the term of this patent is extended or adjusted under 35 U.S.C. 154(b) by 0 days.

(21) Appl. No.: 15/078,464

(22) Filed: Mar. 23, 2016

(65) Prior Publication Data

US 2016/0216285 A1 Jul. 28, 2016

Related U.S. Application Data

(63) Continuation of application No. PCT/JP2014/075625, filed on Sep. 26, 2014.

(30) Foreign Application Priority Data

Sep. 26, 2013 (JP) ................. 2013-199301

(51) Int. Cl.
*G01N 35/00* (2006.01)
*G01N 35/04* (2006.01)

(52) U.S. Cl.
CPC ....... *G01N 35/00029* (2013.01); *G01N 35/04* (2013.01); *G01N 35/0099* (2013.01); *G01N 2035/00059* (2013.01); *G01N 2035/00108* (2013.01); *G01N 2035/00118* (2013.01)

(58) Field of Classification Search
CPC .......... G01N 2035/00059; G01N 2035/00108; G01N 2035/00118
See application file for complete search history.

(56) References Cited

U.S. PATENT DOCUMENTS 4,876,204 A * 10/1989 Inoue ............... G01N 35/00029
422/63
5,540,887 A 7/1996 Yokota et al.
(Continued)

FOREIGN PATENT DOCUMENTS

| CN | 1788943 A | 6/2006 |
|----|-----------|--------|
| JP | H07-311203 | 11/1995 |
| JP | 9-325152 A | 12/1997 |

(Continued)

OTHER PUBLICATIONS

Machine-generated English translation of JP 09325152.*

*Primary Examiner* — Kathryn Wright
(74) *Attorney, Agent, or Firm* — Brinks Gilson & Lione

(57) ABSTRACT

Disclosed is a test strip pickup mechanism configured to pick up test strips for liquid sample analysis one by one from a test strip bottle, the test strip pickup mechanism including: a pickup head configured to suck and hold a test strip; and a motor for rotating the pickup head, wherein the pickup head is provided with a suction hole for sucking and holding the test strip, and the motor is a hollow motor, a hollow portion thereof being connected to the suction hole.

11 Claims, 7 Drawing Sheets

(56) References Cited

U.S. PATENT DOCUMENTS

2001/0019934 A1  9/2001  Nishimura et al.
2006/0133918 A1  6/2006  Akaha

FOREIGN PATENT DOCUMENTS

| | | | |
|---|---|---|---|
| JP | 2686202 | * | 12/1997 |
| JP | 09325152 A | * | 12/1997 |
| JP | H10-329012 | | 12/1998 |
| JP | 3697535 B2 | | 9/2005 |
| JP | 2006-167864 A | | 6/2006 |

* cited by examiner

TEST STRIP PICKUP MECHANISM, TEST STRIP MOVING APPARATUS, LIQUID SAMPLE ANALYZER, AND TEST STRIP PICKUP METHOD

RELATED APPLICATIONS

This application is a continuation of PCT/JP2014/075625 filed Sep. 26, 2014, which claims benefit of Japanese patent application No. 2013-199301 filed Sep. 26, 2013, the content of which are incorporated herein by reference in their entireties.

BACKGROUND OF THE INVENTION

1. Field of the Invention

The present invention relates to a test strip pickup mechanism, a test strip moving apparatus, a liquid sample analyzer, and a test strip pickup method, each for picking up one by one test strips to be used in analysis in a laboratory test on a liquid sample such as urine or blood, especially a urine sample, from a test strip bottle (container) containing a large number of the test strips, and for supplying the test strips to a measurement unit.

2. Description of the Related Art

Urinalysis, for which samples can be easily collected and the result of which can be obtained in a short time, is important as a screening test such as renal function test and diabetes diagnosis, and is an essential test item for mass medical examinations such as school children medical examinations and employee medical examinations. In the case of mass medical examinations, since the number of samples is large, such samples are processed by a continuous automatic analyzer. For speedup of the measurement, it is necessary to efficiently pick up each test strip from a container and to supply the test strip to a measurement unit.

To date, as a type of such supplying apparatus, the invention according to Japanese Patent No. 3697535 which has been devised by the present inventors and for which a patent has been obtained is known. The apparatus according to Japanese Patent No. 3697535 is a test strip pickup mechanism in which a test strip pickup head configured to suck and hold a grip portion of each test strip is provided with a light detector for performing front/back face determination on the grip portion whose front face and back face have at least partially different reflectances, and in which the test strip pickup head is supported in a rotatable manner which allows reversal of the face of the test strip.

The apparatus according to Japanese Patent No. 3697535 allows easy front/back face determination, and can rotate the test strip in accordance with the determination.

However, in the apparatus according to Japanese Patent No. 3697535, since a transmission mechanism such as a belt and a pulley are interposed between the test strip pickup head and a pulse motor, the mechanism is complicated and large.

Urinalysis and blood test which use test strips are more and more conducted at small private medical institutions, and introduction of automatic testing apparatuses is being promoted. At small medical institutions, apparatuses as small as possible are preferred.

SUMMARY OF THE INVENTION

The scope of the present invention is defined solely by the appended claims, and is not affected to any degree by the statements within this summary.

The present invention according to a first aspect is a test strip pickup mechanism configured to pick up test strips for liquid sample analysis one by one from a test strip bottle, the test strip pickup mechanism including: a pickup head configured to suck and hold a test strip; and a motor for rotating the pickup head, wherein the pickup head is provided with a suction hole for sucking and holding the test strip, and the motor is a hollow motor, a hollow portion thereof being connected to the suction hole.

The present invention according to a second aspect is a test strip moving apparatus including: the test strip pickup mechanism described above; an up-down transporter configured to rotatably support the test strip pickup mechanism; a support post configured to support the up-down transporter so as to be movable upward and downward; and a front/back face determination mechanism configured to determine whether a face of the test strip is a front face or a back face.

The present invention according to a third aspect is a liquid sample analyzer including: a test strip moving apparatus configured to pick up test strips for liquid sample analysis one by one from a test strip bottle, and to place the test strip on a test strip placement part with a front face and a back face of the test strip respectively facing predetermined directions; a processing unit configured to apply a liquid sample to the test strip placed on the test strip placement part; and a measurement unit configured to measure the test strip to which the liquid sample has been applied, wherein the test strip moving apparatus includes: a pickup head configured to suck and hold the test strip; and a motor for rotating the pickup head, the pickup head is provided with a suction hole for sucking and holding the test strip, and the motor is a hollow motor, a hollow portion thereof being connected to the suction hole.

The present invention according to a fourth aspect is a test strip moving apparatus including: a test strip pickup mechanism comprising: a pickup head capable of holding a test strip at an distal end of the pickup head; and a hollow motor for rotating the pickup head about an axis extending in a longitudinal direction of the held test strip; a support post extending in an up-down direction; an up-down transporter which is supported so as to be movable upward and downward along the support post, and which supports the test strip pickup mechanism so as to be rotatable relative to the support post in a pendulum manner; and a front/back face determination mechanism disposed so as to face the test strip which has been held and picked up from a test strip bottle by the test strip pickup mechanism, and which has been rotated by a predetermined angle in the pendulum manner, the front/back face determination mechanism determining whether a face of the test strip is a front face or a back face.

The present invention according to a fifth aspect is a test strip pickup method including: holding a test strip contained in a test strip bottle, at an distal end of a pickup head; picking up the held test strip from the test strip bottle; determining, by a front/back face determination mechanism, whether a face of the held test strip is a front face or a back face; and turning the test strip, by a hollow motor connected to the pickup head, when the test strip is held with the front face and the back face reversed.

Here, the test strip is an elongate paper or plastic stick in which reagent layers are provided on one end side of one face of the stick and the other end side of the stick is used as a grip portion. The face provided with the reagent layers is the front face. The front face and the back face of the grip portion have different reflectances in at least parts thereof. For example, in the case of a plastic stick, the surface of an opaque white material is exposed on one face of the plastic stick, and a character, a logo mark, a bar code, or a solid pattern is printed (colored) on the other face, whereby the reflectances of the faces can be changed from each other. The front face and the back face may be provided with printings in colors that have different reflectances, respectively. If a surface of the grip portion is provided with a printing, it is convenient in that the manufacturer name or the type of the test strip, in addition to the colors and the number of the reagent layers, can be readily read.

The liquid sample is a liquid to be subjected to test, preferably a liquid collected from a subject, and is urine or blood, for example. Of course, the liquid sample may be another liquid. The test strip bottle usually is a bottle that can hold therein a large number of (10 or more) test strips vertically.

The pickup head is a portion that holds the test strip. The pickup head preferably holds the test strip by sucking it. The pickup head is provided with: a groove portion for specifying the position at which to hold the test strip; and a suction hole for sucking air. The test strip is fitted in this groove portion, and then is sucked through suction of air via the suction hole, thereby to be held at the pickup head.

That is, the test strip is sucked by a pump to be attracted to and held at the pickup head. The suction hole is connected to the pump by means of a suction tube. The suction tube is preferably made of flexible rubber or plastic, but may be made of a hard material.

A motor for rotating the pickup head is directly connected to the pickup head, without any belt or pulley interposed therebetween. This motor rotates the pickup head to reverse the face of the test strip. This motor is fixed to another member. That this motor is a hollow motor is one feature of the present invention.

The hollow motor is a motor whose center portion in the rotation axis direction is hollow. That is, the shaft which rotates by being driven by a motor is hollow. Gas, liquid, signal wires, and the like can be passed through this hollow portion. The shaft is fixed to the pickup head. When the shaft is rotated, the pickup head is rotated. In a preferable embodiment, a suction tube in communication with the suction hole of the pickup head is disposed inside the hollow portion. The hollow portion is in communication with an L-shaped coupling. The suction tube is connected to the pump through the hollow portion and the L-shaped coupling. Accordingly, even when the pickup head is rotated, the suction tube is not twisted, and thus, blockage or damage of the suction tube can be prevented. Accordingly, this structure is simple compared with a structure where the suction tube is disposed outside the motor. The rotation axis of this motor is parallel to the longitudinal direction of the pickup head.

The test strip pickup mechanism is a mechanism for holding one test strip present in the test strip bottle and lifting the test strip.

A first mode of the present invention is this test strip pickup mechanism, and it is sufficient that the requirements described above are satisfied. Moreover, a moving method therefor is not limited to the one described below, but may be another method. For example, the head may be mounted to the distal end of an arm of a robot, the head may be rotatably supported by a support axis, and this support axis may be driven in front-back, up-down, and left-right directions.

Next, the test strip moving apparatus will be described. The test strip moving apparatus places the held test strip on a test strip placement part. If the test strip is placed on the test strip placement part with the front face and the back face respectively facing predetermined directions, a liquid sample is applied to the test strip by an appropriate apparatus, and the test strip is subjected to measurement.

The test strip moving apparatus includes: the test strip pickup mechanism described above; an up-down transporter; a support post; and a front/back face determination mechanism.

The up-down transporter is a portion that holds the test strip pickup mechanism. The up-down transporter is supported at one end side thereof by the support post and supports on the other end thereof the test strip pickup mechanism. The up-down transporter includes a motor for rotating the test strip pickup mechanism about a horizontal axis (with its plane of rotation set to be substantially vertical). This motor is not for reversing the face of the test strip, but for rotating the test strip pickup mechanism relative to the support post in a pendulum manner to change the angle of the test strip pickup mechanism relative to the support post. By being driven by the motor, the test strip pickup mechanism is located at an angle at which the test strip is sucked and held, at an angle at which the front/back face determination mechanism determines whether a face of the test strip is the front face or the back face, or at an angle at which the test strip is placed at the test strip placement part.

The support post is a post that supports the up-down transporter so as to be movable upward and downward. Any mechanism may be employed for causing the up-down transporter to move up and down. A rack-pinion system, a screw-nut system, or further, another system may be employed.

The front/back face determination mechanism is a mechanism for determining whether a face of the test strip held by the test strip pickup mechanism is the front face or the back face. The front/back face determination mechanism includes a light source and a light receiver (light detector). As the front/back face determination mechanism, for example, a mechanism composed of a light emitting diode and a reflective phototransistor integrated together is preferable. As the front/back face determination mechanism, a light source and a light receiver separated from each other may be used. The light receiver measures reflectance of the grip portion of the test strip. An analytical device connected to the light receiver determines whether the face of the test strip is the front face or the back face on the basis of the magnitude of the reflectance. That is, the analytical device compares the measured reflectance with a previously set threshold value, thereby making the front/back face determination. The analytical device may be a computer or a programmed gate array.

It is sufficient that the setting place of the front/back face determination mechanism is a place where light from the light source hits the grip portion of the test strip as a result of upward-downward movement and rotation of the test strip pickup mechanism by the up-down transporter, and where reflected light can be measured by the light receiver. However, the front/back face determination mechanism is ensured not to come into contact with the test strip placement part described above. That is, the front/back face determination mechanism and the test strip placement part are disposed in a positional relationship in which the test strip can reach the front/back face determination mechanism and the test strip placement part without any interference thereamong, as a result of the upward-downward movement and rotation by the up-down transporter.

The front/back face determination described above is performed while the test strip pickup head is transporting the test strip picked up from the test strip bottle, to the test strip placement part. When the test strip is held with the front face and the back face reversed, the test strip pickup head is rotated during the transportation, such that the test strip is to be placed on the test strip placement part with the reagent portion of the test strip facing upward.

DETAILED DESCRIPTION OF THE PREFERRED EMBODIMENTS

Figure 1:
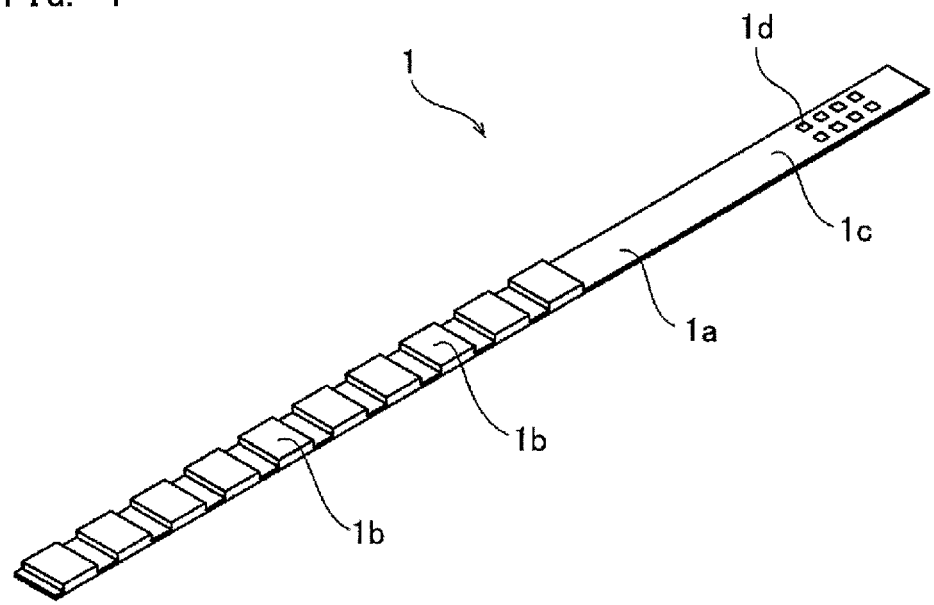
FIG. 1 is a perspective view showing one example of a test strip.

Next, an embodiment in one example will be described in further detail with reference to the drawings. FIG. 1 shows one example of a test strip. The test strip 1 is a test strip for qualitative examination of components contained in urine. Examples of the components include occult blood, protein, glucose, ketone body, and the like. The test strip 1 is an elongate opaque white plastic stick 1a which has a plurality of reagent layers 1b on one end side thereof and which has a grip portion 1c on the other end thereof. The face provided with the reagent layers 1b is the front face, and a logo mark 1d is printed on a portion of the grip portion 1c. The plurality of reagent layers 1b respectively correspond to the items such as occult blood, protein, and the like.

Figure 2:
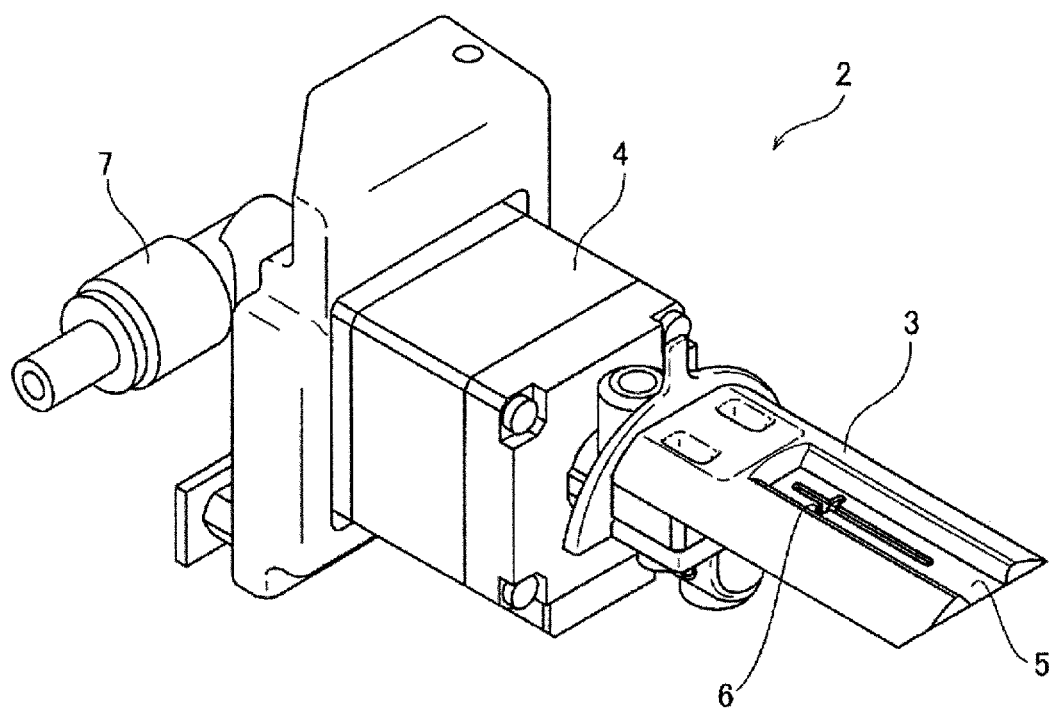
FIG. 2 is a perspective view showing one example of a test strip pickup mechanism.

FIG. 2 shows one example of a test strip pickup mechanism 2. The test strip pickup mechanism 2 includes a pickup head 3 and a hollow motor 4. The pickup head 3 has a groove portion 5 into which a test strip is to be fitted in. In the groove portion 5, a suction hole 6 for sucking the test strip is provided. By the grip portion 1c being fitted in the groove portion 5, the long side of the test strip 1 is held along the longitudinal direction of the groove portion 5.

The cavity continued from the suction hole 6 is connected to the hollow portion of the hollow motor 4, and an L-shaped coupling 7 is connected to the hollow portion. Inside the hollow portion and the L-shaped coupling 7, a suction tube which connects the suction hole 6 to the pump is disposed.

Figure 3:
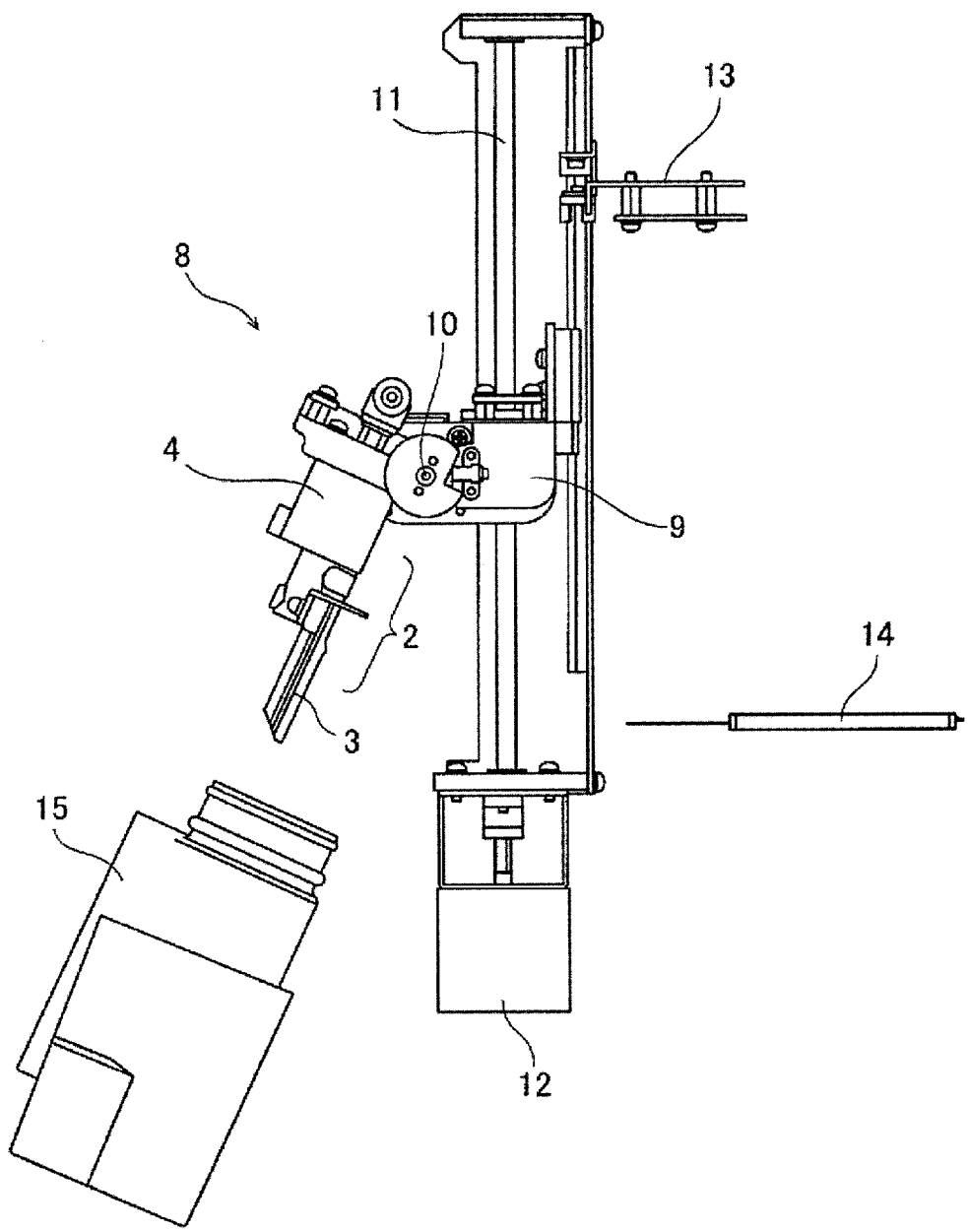
FIG. 3 is a side view showing one example of a test strip moving apparatus.

FIG. 3 is a side view showing one example of a test strip moving apparatus 8. The test strip pickup mechanism 2 having the pickup head 3 is fixed to an up-down transporter 9. The up-down transporter 9 is provided with a motor 10 for rotating the test strip pickup mechanism 2 (along a plane parallel to the face of this drawing sheet) relative to a support post 11 in a pendulum manner. Further, the up-down transporter 9 is supported by the support post 11 so as to be movable upward and downward. A motor 12 is connected to the support post 11. The support post 11 and the up-down transporter 9 are in a screw-nut relationship. The support post 11 is rotated by being driven by the motor 12, whereby the up-down transporter 9 moves upward or downward.

A front/back face determination mechanism 13 is disposed above. A test strip placement part 14 is disposed below the front/back face determination mechanism 13. A test strip bottle 15 is located at the lower left in this drawing. In this example, the test strip bottle 15 is slightly inclined (about 20 to 30 degrees from the vertical direction). This is for facilitating picking up the test strip.

As seen from this example, since the shaft of the hollow motor 4 is directly connected to the pickup head 3, there is no complicated force transmission mechanism between the hollow motor 4 and the pickup head 3. Further, in this example, there are no moving apparatuses that move in front-back and left-right directions. This also greatly reduces necessary parts and space.

Figure 4:
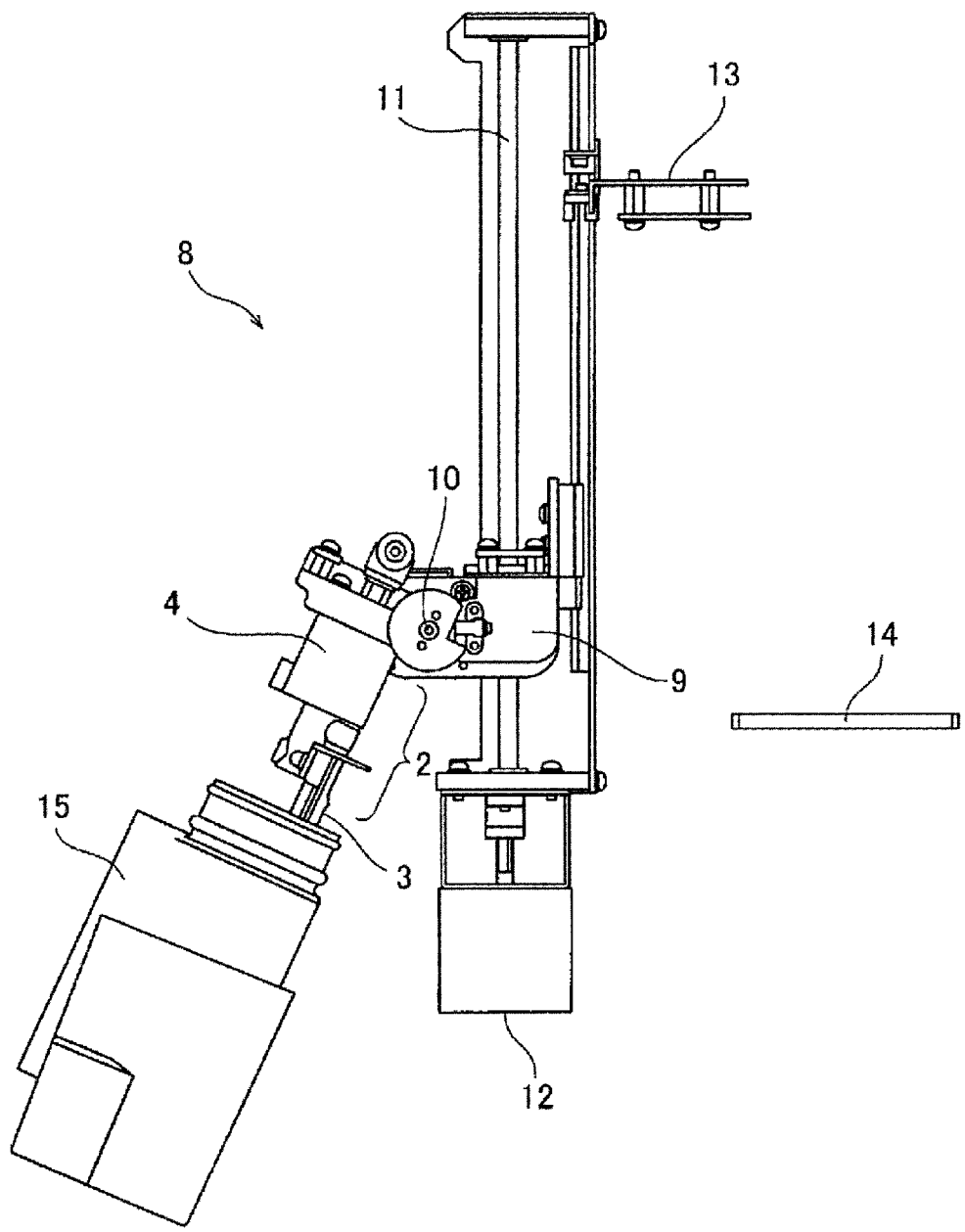
FIG. 4 is a side view showing one example of the test strip moving apparatus.
Figure 5:
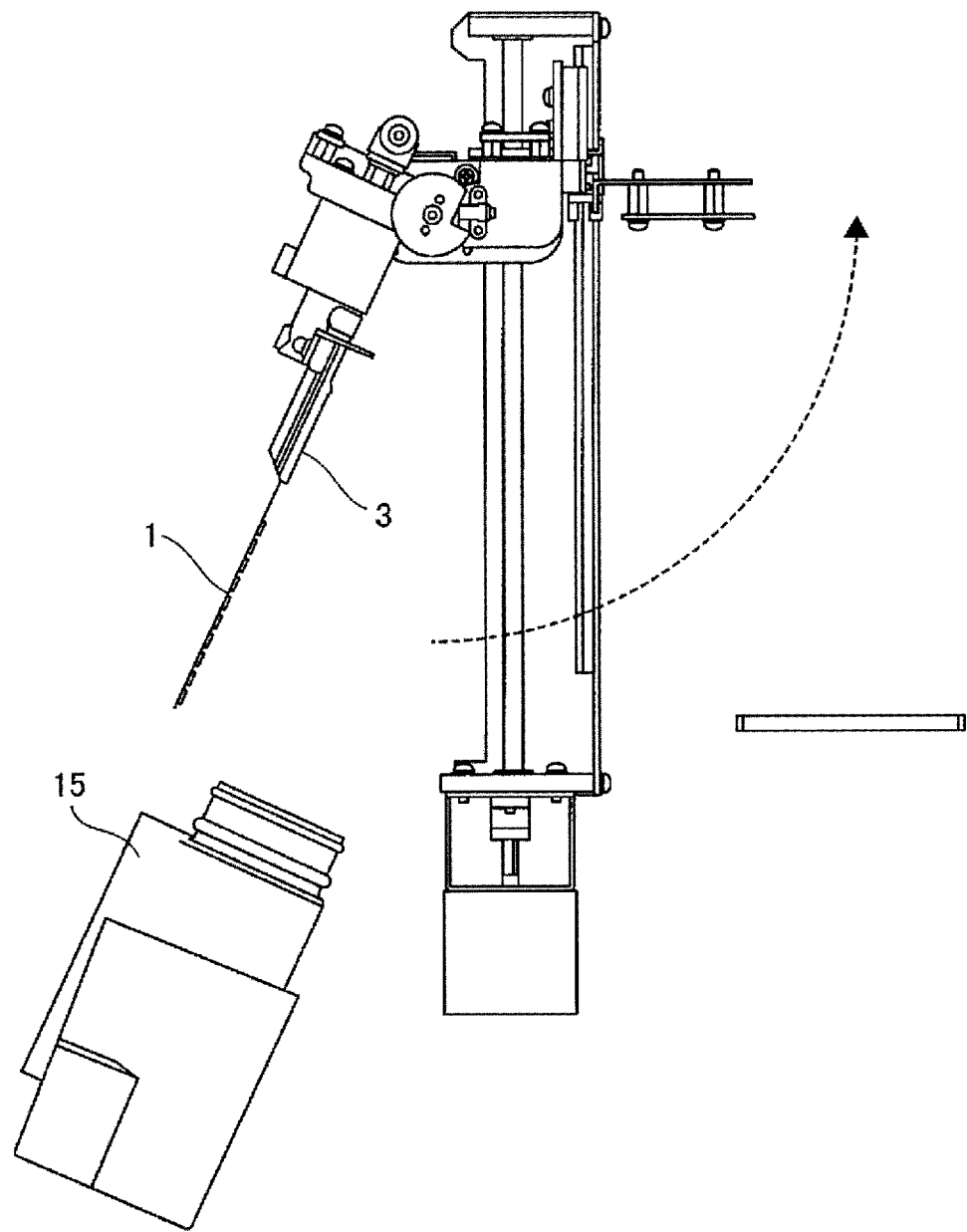
FIG. 5 is a side view showing one example of the test strip moving apparatus.
Figure 6:
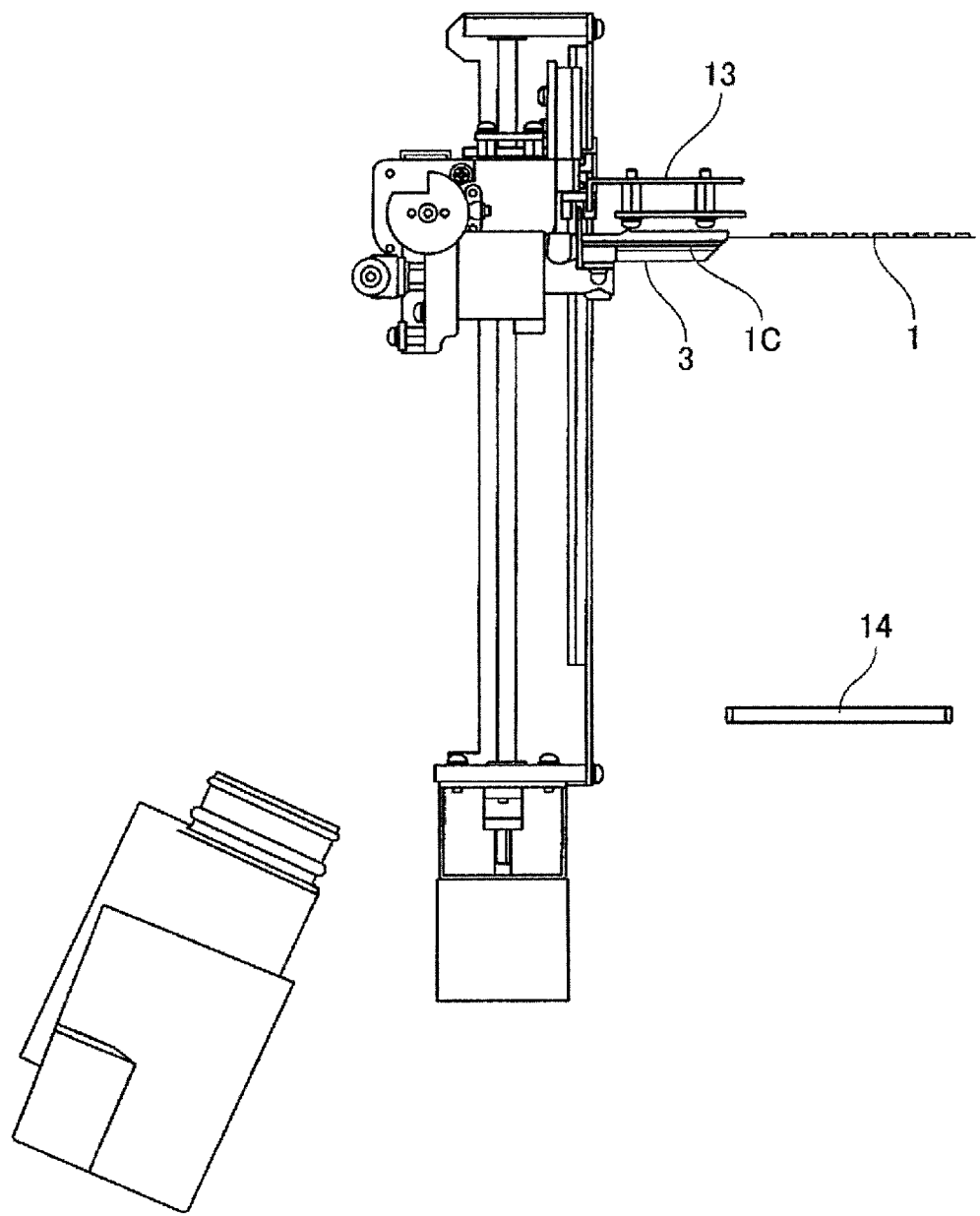
FIG. 6 is a side view showing one example of the test strip moving apparatus.

FIG. 4 indicates that: the pickup head 3 having entered the test strip bottle 15 is approaching a test strip 1 while sucking air through the suction hole 6; and the pickup head 3 is fitting the test strip 1 into the groove portion 5 with the suction force. From this state, when the up-down transporter 9 has moved upward as shown in FIG. 5, the test strip 1 is picked up from the test strip bottle 15. FIG. 5 shows a state where the test strip 1 has been picked out. From this state, the test strip pickup mechanism 2 is rotated along the broken line arrow by being driven by the motor 10, whereby the state shown in FIG. 6 is realized. The broken line arrow is the trajectory of the tip of the test strip 1. From this figure, it is seen that the test strip 1 can be located at the front/back face determination mechanism 13 without getting into contact with the test strip placement part 14.

FIG. 6 indicates that the front/back face determination mechanism 13 is determining whether a face of the test strip 1 is the front face or the back face. The grip portion 1c of the test strip 1 has just come close to the front/back face determination mechanism 13. As a result of the front/back face determination, if the face on the upper side (the rear face of the face sucked by the pickup head 3) of the test strip 1 in FIG. 6 is the front face, the up-down transporter 9 is lowered and the test strip 1 is placed on the test strip placement part 14. On the other hand, if the face on the upper side of the test strip 1 is the back face, the pickup head 3 is rotated while the up-down transporter 9 is lowered, and the face of the test strip 1 is reversed. The reversed test strip 1 is placed on the test strip placement part 14.

Figure 7:
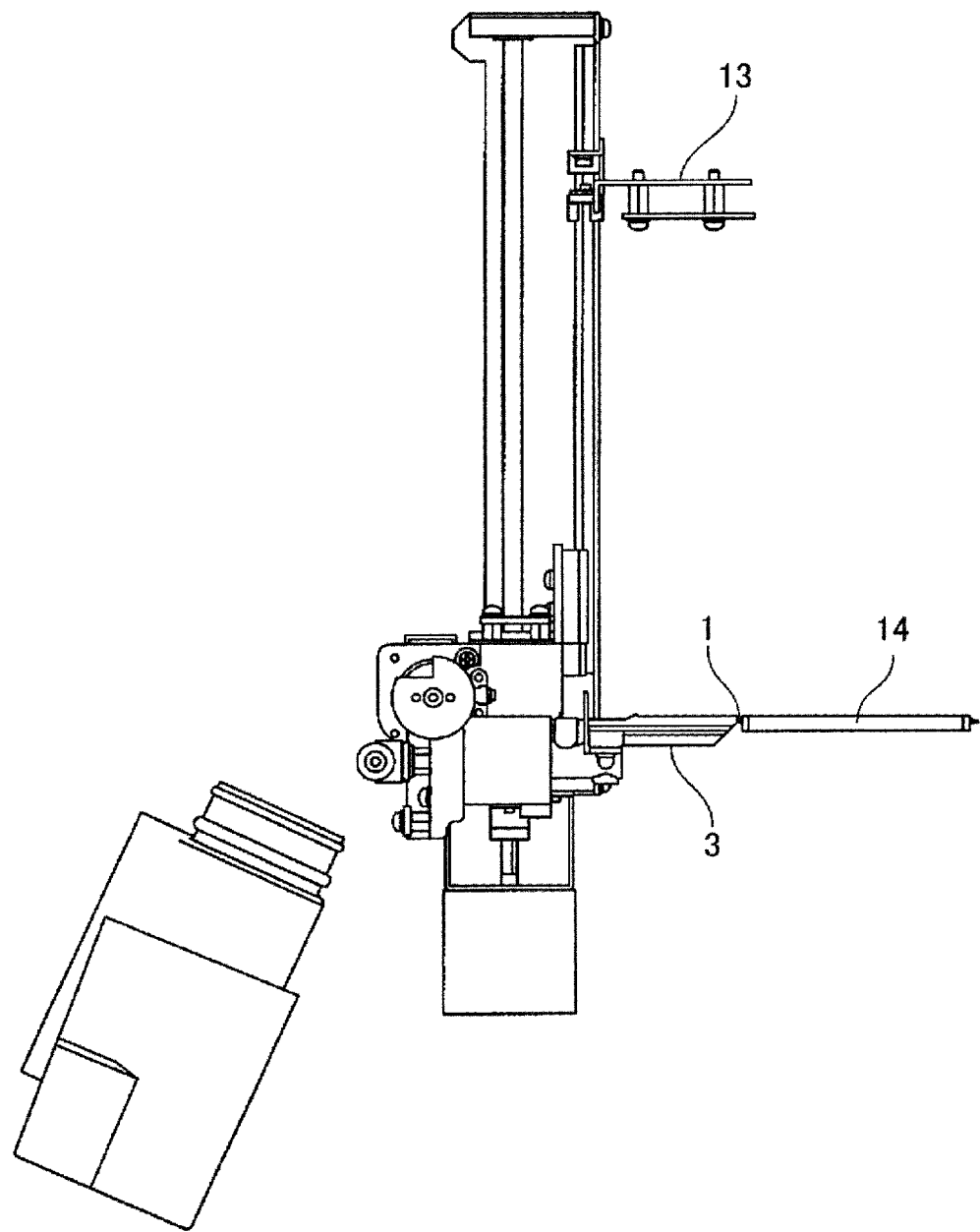
FIG. 7 is a side view showing one example of the test strip moving apparatus.

FIG. 7 indicates that the up-down transporter 9 having been lowered from the position shown in FIG. 6 is placing the test strip 1 on the test strip placement part 14. If the suction is stopped after the test strip 1 has been placed, the test strip 1 is released, and steps thereafter can be performed.

Figure 8:
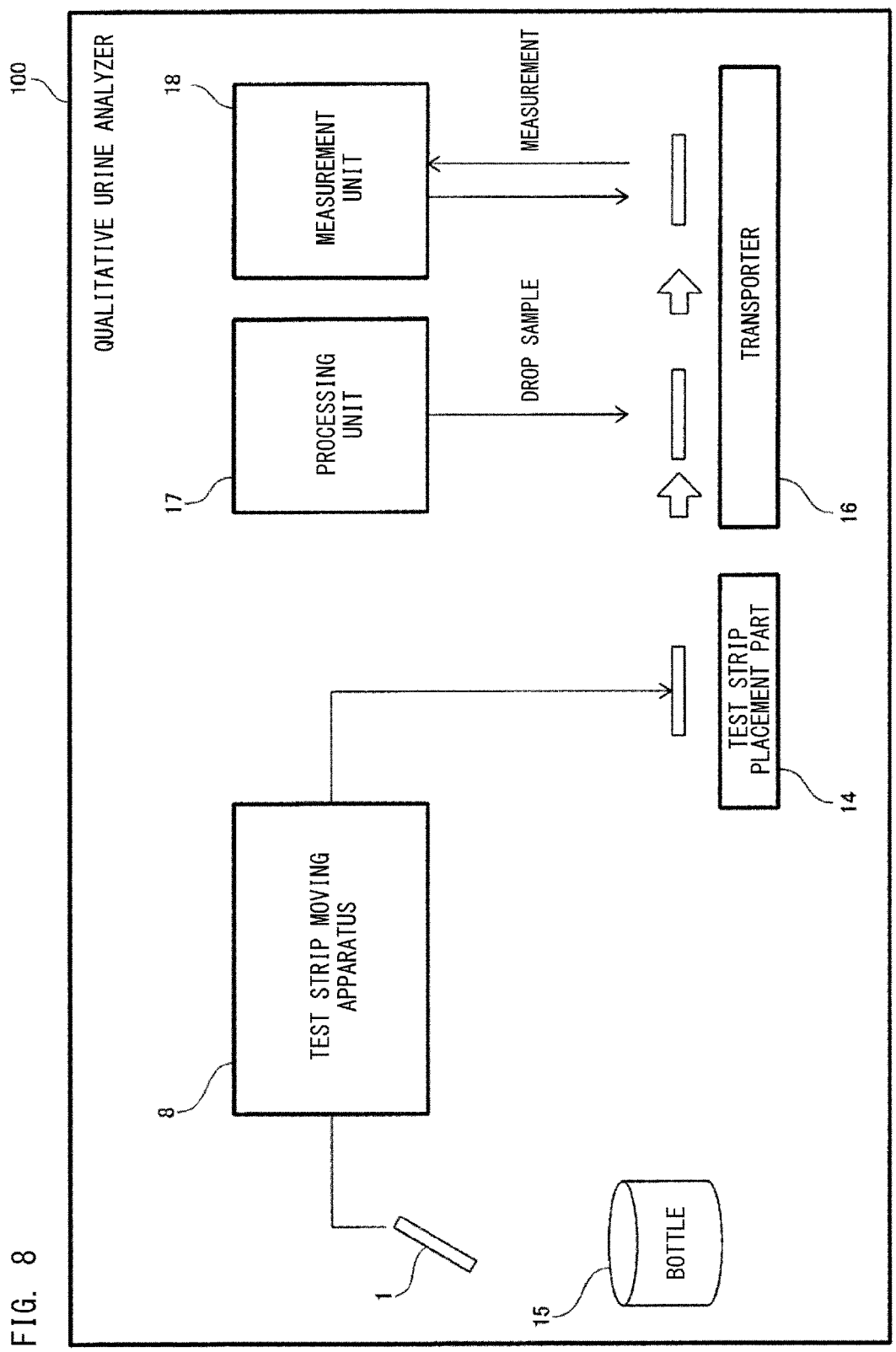
FIG. 8 is a block diagram showing one example of a qualitative urine analyzer.

FIG. 8 is a block diagram showing a configuration of a qualitative urine analyzer 100. A test strip 1 picked up from the test strip bottle 15 by the test strip moving apparatus 8 and placed on the test strip placement part 14 is sequentially transported by a transporter 16, to a processing unit 17 and a measurement unit 18. In a preferred embodiment, the transporter 16 is a belt conveyor that transports the test strip 1 along the longitudinal direction. The processing unit 17 drops a urine sample on the reagent layers 1b of the transported test strip 1. The measurement unit 18 optically reads change in color of each reagent layer 1b onto which the urine sample has been dropped. Accordingly, the content of the measurement item (component) corresponding to each reagent layer 1b is qualitatively measured. The measurement result is classified as (−), (+), (++), or the like, in accordance with the degree of change in color of each reagent layer 1b, and is reported as an analysis result.

The embodiment has the effects described below.

(1) A commercially-available test strip bottle in a state where test strips are contained therein can be used as it is. Thus, operation of transferring the test strips into a dedicated container or hopper is not necessary, which is labor-saving, and contamination of the test strips associated with the transfer is prevented.

(2) Since front/back face determination and reversal of the face of each of the test strips picked up one by one by the test strip pickup head can be performed while the test strip is being transported to the test strip placement part, time necessary for the determination and reversal can be shortened.

(3) Since the motor for reversing the face of the test strip is a hollow motor, the test strip pickup mechanism is very compact and thus easy to be used in an analyzer for small medical institutions and small test institutions.

What is claimed is:

1. A test strip pickup apparatus configured to pick up a test strip for liquid sample analysis, the test strip pickup apparatus comprising:
    a support post standing straight in a height direction;
    a transporter movable along the support post in opposite ways along the height direction;
    a motor fixedly attached to the transporter and movable, along with movement of the transporter, in the opposite ways along the height direction, the motor being rotatable about a first axis extending in orthogonal to a vertical plane defined by a pair of mutually orthogonal axes one axis of which extends in parallel to the height direction, and the other of which extends in orthogonal to the height direction;
    a hollow motor rotationally movable, along with rotation of the motor, around the first axis in parallel to the vertical plane, the hollow motor being rotatable about a second axis extending in parallel to the vertical plane, the second axis being rotationally movable, along with rotation of the motor, around the first axis while remaining in parallel to the vertical plane; and
    a pickup head operably connected to the hollow motor and rotatable, along with rotation of the hollow motor, about the second axis, the pickup head being rotationally movable, along with rotation of the motor, around the first axis while remaining in parallel to the vertical plane, the pickup head being formed with a groove extending in parallel with the vertical plane, the groove being provided with a suction hole and operable to hold a test strip in the groove by operation of negative air pressure through the suction hole,
    wherein the test strip has degrees of freedom in motion which are limited to three degrees in which the test strip (i) rotates around the second axis in the vertical plane, (ii) rotationally moves around the first axis in parallel to the vertical plane and (iii) moves straight in the opposite ways along the height direction in the vertical plane, and
    further wherein the test strip has a front face and a back face opposite to the front face, and the test strip pickup apparatus further comprises a front/back face determination mechanism configured to determine whether the test strip is held with the front face down or up in the groove, and
    the front face and the back face of the test strip have different light reflectances, and the front/back face determination mechanism comprises a light source and a light receiver operable to measure a reflectance of a face of the test strip facing the light source.

2. The test strip pickup apparatus of claim 1, wherein the test strip has a longitudinal length and being held in the groove so that the longitudinal length of the test strip extends along the groove in parallel to the second axis and the vertical plane.

3. The test strip pickup apparatus of claim 1, wherein the hollow motor is formed with a hollow portion communicating the negative air pressure with the suction hole.

4. The test strip pickup apparatus of claim 1, wherein
    the pickup head is rotationally movable, along with rotation of the motor, around the first axis, while remaining in parallel to the vertical plane, between a first angular position and a second angular position, the first and second angular positions being located on opposite sides of the support post,
    the pickup head is movable, along with movement of the transporter, along the height direction between a first height position and a second height position located above the first height position,
    the pickup head is movable, along with rotation of the motor and movement of the transporter, between a pickup location, defined at the first angular position and the first height position, where the pickup head picks up the test strip from a test strip bottle, and an inspection location, defined at the second angular position and the second height position, where the pickup head presents the test strip held thereby to the front/back face determination mechanism to determine whether the test strip is held by the groove with the front face down or up in the groove.

5. The test strip moving apparatus of claim 1, wherein
    the pickup head is movable, along with movement of the transporter, along the height direction between the second height position and a third height position located below the first height position, and
    the pickup head is movable, along with movement of the transporter, along the height direction from the inspection location to an unloading location, defined at the second angular position and the third height position, where the pickup head unloads the test strip onto a test strip placement part.

6. The test strip pickup apparatus of claim 1, wherein the hollow motor is operable to rotate the pickup head by 180 degrees to flip the test strip in the groove upside down, depending on a determination by the front/back face determination mechanism as to whether the test strip is held with the front face down or up in the groove.

7. A liquid sample analyzer comprising:
    a test strip pickup apparatus configured to pick up a test strip for liquid sample analysis and to place the test strip on a test strip placement part;
    a processing unit configured to apply a liquid sample to the test strip placed on the test strip placement part; and
    a measurement unit configured to test the test strip to which the liquid sample is applied, wherein the test strip pickup apparatus comprises:
        a support post standing straight in a height direction;
        a transporter movable along the support post in opposite ways along the height direction;
        a motor fixedly attached to the transporter and movable, along with movement of the transporter, in the opposite ways along the height direction, the motor being rotatable about a first axis extending in orthogonal to a vertical plane defined by a pair of mutually orthogonal axes one axis of which extends in parallel to the height direction, and the other of which extends in orthogonal to the height direction;

a hollow motor rotationally movable, along with rotation of the motor, around the first axis in parallel to the vertical plane, the hollow motor being rotatable about a second axis extending in parallel to the vertical plane, the second axis being rotationally movable, along with rotation of the motor, around the first axis while remaining in parallel to the vertical plane; and a pickup head operably connected to the hollow motor and rotatable, along with rotation of the hollow motor, about the second axis, the pickup head being rotationally movable, along with rotation of the motor, around the first axis while remaining in parallel to the vertical plane, the pickup head being formed with a groove extending in parallel with the vertical plane, the groove being provided with a suction hole and operable to hold a test strip in the groove by operation of negative air pressure through the suction hole, wherein the test strip has degrees of freedom in motion which are limited to three degrees in which the test strip (i) rotates around the second axis in the vertical plane, (ii) rotationally moves around the first axis in parallel to the vertical plane and (iii) moves straight in the opposite ways along the height direction in the vertical plane, and further wherein the test strip has a front face and a back face opposite to the front face, and the test strip pickup apparatus further comprises a front/back face determination mechanism configured to determine whether the test strip is held with the front face down or up in the groove, and the front face and the back face of the test strip have different light reflectances, and the front/back face determination mechanism comprises a light source and a light receiver operable to measure a reflectance of a face of the test strip facing the light source.

8. The liquid sample analyzer of claim 7, wherein the test strip is a test strip to be used in a qualitative urine test, and the liquid sample analyzer is a qualitative urine analyzer.

9. The liquid sample analyzer of claim 7, wherein the hollow motor is formed with a hollow portion communicating the negative air pressure with the suction hole.

10. A test strip pickup method comprising:

moving a pickup head straight down along a support post in a height direction from a first height position to a second height position located below the first height position;

rotationally moving the pickup head in parallel to a vertical plane to a first angular position about a first axis extending in orthogonal to the vertical plane, the vertical plane being defined by a pair of mutually orthogonal axes one axis of which extends in parallel to the height direction, and the other of which extends in orthogonal to the height direction;

positioning the pickup head at a pickup location defined at the second height position and the first angular position;

picking up a test strip from a test strip bottle with the pickup head at the pickup location by operation of negative air pressure;

moving the pickup head straight up along the support post in the height direction from the second height position to a third height position located above the second height position, rotationally moving the pickup head to a second angular position about the first axis in parallel to the vertical plane, the first and second angular positions being located on opposite sides of the support post;

presenting the test strip, held by the pickup head, at an inspection location where the test strip is inspected as to whether the test strip is held by the pickup head with a front face thereof up or down, wherein the test strip has a back face opposite to the front face, and the front face and the back face of the test strip have different light reflectances;

irradiating with a light source to measure a reflectance of a face of the test strip facing the light source;

determining whether the test strip is held with the front face down or up in the groove;

upon a determination that the test strip is held upside down, rotating the pickup head about a second axis extending in parallel to the vertical plane to flip the test strip held by the pickup head;

moving the pickup head straight down along the support post in the height direction from the third height position to a fourth height position located below the second height position; and unloading the test strip from the pickup head onto a placement part at an unloading location defined at the second angular position and the fourth height position, wherein the test strip has degrees of freedom in motion which are limited to three degrees in which the test strip (i) rotates around the second axis in the vertical plane, (ii) rotationally moves around the first axis in parallel to the vertical plane and (iii) moves straight in the opposite ways along the height direction in the vertical plane.

11. The test strip pick up method of claim 10, wherein the test strip is a test strip to be used in a qualitative urine test.

* * * * *